United States Patent [19]
Elgavish

[11] Patent Number: 5,824,493
[45] Date of Patent: Oct. 20, 1998

[54] DIAGNOSTIC TEST FOR INTERSTITIAL CYSTITIS

[75] Inventor: Ada Elgavish, Birmingham, Ala.

[73] Assignee: University of Alabama Research Foundation, Birmingham, Ala.

[21] Appl. No.: 604,810

[22] Filed: Feb. 23, 1996

[51] Int. Cl.[6] .............................. C12Q 1/02; C12Q 1/04; G01N 33/53; G01N 33/20

[52] U.S. Cl. .......................... 435/29; 435/7.2; 435/7.21; 435/7.1; 435/34; 435/378; 435/377; 435/374; 435/383; 435/404; 435/391; 435/29; 435/30; 424/558; 436/74; 436/63

[58] Field of Search .............................. 435/29, 7.2, 7.21, 435/240.2, 240.21, 34, 7.1, 378, 374, 383, 404, 391, 30; 424/558; 436/74, 63

[56] References Cited

U.S. PATENT DOCUMENTS

| | | | |
|---|---|---|---|
| 4,643,971 | 2/1987 | Fradet et al. | 435/29 |
| 5,039,611 | 8/1991 | Fradet | 435/29 |
| 5,234,698 | 8/1993 | Fahim | 435/29 |
| 5,318,891 | 6/1994 | Elgebaly | 435/29 |

*Primary Examiner*—Louise Leary
*Attorney, Agent, or Firm*—Benjamin Aaron Adler; McGregor & Adler, P.C.

[57] ABSTRACT

A method of diagnosing interstitial cystitits in an individual and a kit for the method, comprising the steps of: obtaining primary cultures of urothelial cells; selecting urothelial cells of basal type and producing secondary cultures; measuring in secondary cultures (1) percentage of single cells and percentage of large colonies; (2) determining proliferative ability; (3) determining differentiation ability; (4) determining the percentage of large colonies that express phosphotyrosine and/or nitrotyrosine; (5) measuring the percentage of apoptotic cells; (6) measuring the percentage of large colonies; and (7) comparing the percentage of the colonies to baseline values of the same parameters determined in samples of similarly cultured urothelial cells taken from individuals not suspected of having interstitial cystitis.

26 Claims, 5 Drawing Sheets

DIAGNOSTIC TEST FOR INTERSTITIAL CYSTITIS

BACKGROUND OF THE INVENTION

1. Field of the Invention

The present invention relates generally to the fields of urology, infectious diseases and diagnostic methodology. More specifically, the present invention relates to a novel diagnostic test for interstitial cystitis.

2. Description of the Related Art

Interstitial cystitis (IC) is a chronic disease of the bladder wall[2,12,26,37,46]. Distention at cystoscopy reveals scars, mucosal splittings and petechial hemorrhages[20,27,40]. Foci of urothelial detachment in bladders from patients with interstitial cystitis suggest that the architecture of the interstitial cystitis bladder urothelium is altered[20]. This possibility is further supported by classical studies relating dysfunction of the interstitial cystitis bladder mucosa with altered expression of proteoglycans on the surface of epithelial cells[33,34].

The etiology of interstitial cystitis is unknown. Its rapid onset, appearance in midlife, and absence of strong family association suggest that interstitial cystitis is an acquired disease, possibly caused by an infectious agent. The fact that 90% of interstitial cystitis patients are women parallels the epidemiology of bacterial urinary tract infections further supporting this possibility[46].

In spite of this evidence, the possibility that bacterial infection is an etiologic factor in interstitial cystitis has been controversial since urine from patients with interstitial cystitis does not consistently grow bacteria in culture[15]. However, bacteria are common inhabitants of the lower urinary tract and urinary bladder infection with these microorganisms may frequently go unnoticed[25,45]. Moreover, some bacteria possess the means to invade into, between or through epithelial cells[50] and remain associated with the injured urothelium, even while absent in the urine[11]. Finally, the fact that pathogenic bacteria cannot be detected consistently in the urine or in the bladder wall of patients with interstitial cystitis does not exclude the possibility that interstitial cystitis may develop in the aftermath of bacterial infection.

Earlier studies were based on the assumption that the sole avenue for the ingress of bacteria into the bladder is exposure of superficial urothelial cells to infectious agents in the lumen. However, existing evidence indicates that urothelial cells in the basal layer have also access to bacteria and their products[11]. For example, *Enterococcus faecalis* can translocate across the intestinal mucosa[50] and this can be an avenue for the ingress of streptococci into other organs, including the inner layers of the bladder urothelium. Altered function of basal urothelial cells is more likely to have long lasting effects on bladder function than that of superficial cells which are shed in response to infectious agents[3] and are replaced by unexposed urothelial cells in layers underneath. Based on these studies, it was presumed that under the infrequent conditions in which bacteria or their toxins have access to poorly differnetiated urothelial cells in the basal layer, e.g., when the bladder urothelium is injured or under conditions of systemic infection[11,19,46,50], bacterial toxin-induced mechanisms lead to the onset of pathological changes characteristic to IC[20,27]. For example, exposure to bacterial products may affect proliferative and differentiation abilities of basal cells with high proliferative potential, i.e., stem bells, causing abnormal urothelial development and altered function of the urothelium, such as has been reported in IC[20,26,27,37,46]. To explore this possibility, two hypotheses were tested in vitro in the present studies: (i) The proliferative ability of basal cells isolated from patients with IC is altered as compared with basal cells from control patients; (ii) The IC phenotype can be induced in vitro by treatment of basal cells from control patients with bacterial products, e.g., lipoteichoic acid from the gram positive *Streptococcus faecalis*.

The prior art is deficient in the lack of effective means of diagnosing interstitial cystitis. The present invention fulfills this longstanding need and desire in the art.

SUMMARY OF THE INVENTION

Interstitial cystitis (IC) is a chronic disease of the urinary bladder wall of unknown etiology. The present invention demonstrates that exposure of basal urothelial cells to bacterial toxins, due to urothelial injury occurring during infection, alters their proliferative and differentiation properties. In vivo, these processes may result in foci of urothelial detachment and mucosal splittings typical to interstitial cystitis. That treatment of poorly differentiated urothelial cells with bacterial toxins inhibits integrin-mediated cell-extracellular matrix interactions support the present invention. In the present invention, the proliferative responses, differentiation abilities and expression of integrins at cell-cell contacts were compared in: (i) untreated urothelial cells isolated from interstitial cystitis bladders (IC); (ii) untreated urothelial cells isolated from control bladders (control); and (iii) urothelial cells from control bladders treated in vitro with lipoteichoic acid from *Streptococcus faecalis* (LT-2).

To simulate conditions in the basal layer of the normal urothelium that restrict proliferation and inhibit terminal differentiation, cell cultures used in the present studies were grown on a collagen-coated or fibronectin-coated substrate, in medium containing low levels of $Ca^{2+}$ and growth factors. Studies in vitro have shown that epithelial proliferation and differentiation, in particular stratification, are inhibited in low $Ca^{2+}$ medium[54]. Under these conditions, secondary cultures of urothelial cells displayed a highly reproducible pattern of colony size distribution. This was consistent with the possibility that colony size distribution in vitro may reflect a constant proliferative potential distribution in the population of progenitor basal urothelial cells in vivo. This suggested that large colonies defined as those consisting of more than 6 cells per colony were progeny of basal cells with high proliferative potential, whereas small colonies were progeny of partially differentiated cells with limited proliferative ability. These possibilities were supported by studies in other tissues indicating that the population of basal epithelial cells abutting the basement membrane consisted of a limited number of cells with high proliferative potential, i.e., stem cells[36], while many of the remaining cells had intermediate proliferative potential[35].

It was next postulated that if the percentage of quiescent cells with high proliferative potential was constant in the basal layer of the urothelium in vivo, the percentage that their progeny, i.e., large colonies, represented in the population of colonies in vitro was likely to be limited and regulated by environmental factors, e.g., growth factors. This possibility was supported by earlier studies in vitro from this laboratory. First, the percentage of large colonies of urothelial cells increased in a dose-dependent manner as a function of levels of growth factors, e.g., bovine pituitary extract (BPE), in the growth medium. Secondly, the percentage of large colonies reached a maximum after 3 days of culture in medium containing 0.05% bovine pituitary extract, as the precentage of large colonies did not increase any further in cultures grown for longer times, or in media containing higher levels of bovine pituitary extract.

The majority of colonies from control bladders consisted of 1–5 cells per colony and a considerable part of these colonies were poorly differentiated and expressed an $\alpha_3\beta_1$ integrin in clusters. This population of colonies, in particular poorly differentiated single cells, was reduced in IC as compared to control. The percentage of control large colonies consisting of 6 or more cells per colony was very low, 3.89±3.78 as compared to 31.08±5.33 in IC cultures. All colonies in the IC group were well differentiated and all expressed an $\alpha_3 b_1$ integrin at cell-cell contacts, as is typical for more differentiated cells of intermediate type. When compared to control, changes almost identical to those found in IC occurred in the LT-2 group. It was concluded that, high lipoteichoic acid (LT) concentrations developing at foci of infection may induce a local subpopulation of basal uroepithelial cells to proceed through proliferation and differentiation at an increased rate. Redistribution of $\beta_1$ integrins at foci of differentiation in the basal layer of the interstitial cystitis urothelium, from structures allowing interaction with the basement membrane to cell-cell contacts, could be a cause for urothelial detachments typical to the interstitial cystitis bladder.

In one embodiment of the present invention, there is provided a method of diagnosing interstitial cystitis in an individual, comprising the steps of: (i) obtaining primary cultures of urothelial cells from bladder biopsies of said individual; (ii) using primary cultures and a growth medium containing low levels of calcium and growth factors (i.e., growth conditions that similate those in the basal layer of the urinary bladder by restricting proliferation and inhibiting terminal differentiation) to select urothelial cells of basal type and produce secondary cultures thereof; (iii) to measure colony size distribution in secondary cultures of basal urothelial cells by examining randomly chosen 100 colonies, determining the number of cells in each colony and dividing the colonies in 7 groups by criterion of number of cells per colony (1,2,3,4,5,6, or more than 6 cells per colony); (iv) to determine percentage of single cells and percentage of large colonies, i.e., the number of single cells and the number of large colonies, repectively, as a percentage of all colonies examined in the secondary culture; (v) to compare percentage of single cells and percentage of large colonies to those in a sample of similarly cultured urothelial cells taken from an individual not suspected of having interstitial cystitis.

In another embodiment of the present invention, there is provided a method of diagnosing interstitial cystitis in an individual, comprising the steps of: (i) obtaining primary cultures of urothelial cells from bladder biopsies of said individual; (ii) using primary cultures and a growth medium containing low levels of calcium and growth factors to select urothelial cells of basal type and produce secondary cultures thereof; (iii) measuring proliferation using bromodeoxyuridine (BrdU) incorporation and a immunocytochemical technique to detect it in cell nuclei; (iv) to determine the percentage of single cells and large colonies that contain at least one BrdU-incorporating (i.e., proliferating) cell; (v) to determine the percentage of large colonies that contain 1,2,3,4,5, or more than 6 BrdU-incorporating cells; (vi) to compare percentage of single cells and large colonies that contain at least one BrdU-incorporating cell, and, the percentage of large colonies that contain 1,2,3,4,5, or more than 6 BrdU-incorporating cells, to that in a sample of similarly cultured urothelial cells taken from an individual not suspected of having interstitial cystitis.

In yet another embodiment of the present invention, there is provided a method of diagnosing interstitial cystitis in an individual, comprising the steps of: (i) obtaining primary cultures of urothelial cells from bladder biopsies of said individual; (ii) using primary cultures and a growth medium containing low levels of calcium and growth factors to select urothelial cells of basal type and produce secondary cultures thereof; (iii) measuring differentiation by probing cells with antibodies against cytokeratin 8, a marker of epithelial differentiation and detecting it by an immunofluorescence microscopy technique; (iv) to determine the percentage of single cells and large colonies that contain at least one intense cytokeratin 8-expressing (i.e., differentiated) cell; (v) to determine the percentage of large colonies that contain 1,2,3,4,5, or more than 6 intense cytokeratin 8-expressing cells; (vi) to compare percentage of single cells and large colonies that contain at least one cytokeratin 8-expressing cell and the percentage of large colonies that contain 1,2,3, 4,5, or more than 6 intense cytokeratin 8-expressing cells to that in a sample of similarly cultured urothelial cells taken from an individual not suspected of having interstitial cystitis.

In yet another embodiment of the present invention, there is provided a method of diagnosing interstitial cystitis in an individual, comprising the steps of: (i) obtaining primary cultures of urothelial cells from bladder biopsies of said individual; (ii) using primary cultures and a growth medium containing low levels of calcium and growth factors to select urothelial cells of basal type and produce secondary cultures thereof; (iii) measuring differentiation by probing cells with antibodies against $\beta_1$ subunit of integrins and exaiming its presence at cell-cell contacts; (iv) to determine the percentage of large colonies that express $\beta_1$ integrin at cell-cell contacts of 2,3,4,5,6, or more than 6 cells; (v) to compare percentage of large colonies that express $\beta_1$ integrin at cell-cell contacts of 2,3,4,5,6, or more than 6 cells to that in a sample of similarity cultured urothelial cells taken from an individual not suspected of having interstitial cystitis.

In yet another embodiment of the present invention, there is provided a method of diagnosing interstitial cystitis in an individual, comprising the steps of: obtaining primary cultures of urothelial cells from bladder biopsies of said individual; using primary cultures and a growth medium containing low levels of calcium and growth factors to select urothelial cells of basal type and produce secondary cultures thereof; measuring the percentage of apoptotic cells in the entire culture; measuring the percentage of large colonies that contain 1,2,3,4,5,6, or more than 6 apoptotic cells; and comparing the percentage of said colonies to baseline values of the same parameters determined in samples of similarly cultured urothelial cells taken from individuals not suspected of having interstitial cystitis.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the distribution of colonies of varying size in cultures of bladder epithelial cells from interstitial cystitis patients (IC) and control subjects (control). Cells were grown on glass cover slips coated with 20 µg/ml fibronectin (FIG. 1A) or collagen (FIG. 1B), in complete F12* medium containing 0.2 mM $Ca^{2+}$ and 0.005% bovine pituitary extract. During the last 3 days of growth in culture, all cell cultures grew in BPE-free, insulin-free F12* medium containing 0.2 mM $Ca^{2+}$. Some of the control cultures received 25 µg/ml lipoteichoic acid from *Streptococcus faecalis* during their last 3 days of growth in culture (LT2); filled bars). The rest of the control (open bars) and IC (hatched bars) cultures grew during their last 3 days in culture in the presence of the vehicle (0.5% ethanol), but no toxin. Cells were then probed with one of several monoclonal, affinity-purified antibodies (against cytokeratin 8, integrin subunits $\alpha_3$, $\beta_1$). A total of 100 randomly chosen colonies were examined in each sample. The number of cells in each colony was determined. For the analysis of results, colonies examined were divided in 10 groups as a function of the number of cells per colony, i.e., 1–10 cells per colony, respectively. The eleventh group consisted of all colonies containing more than 10 cells per colony. Results are expressed as means±standard deviation of colonies consisting of the respective number of cells per colony as a percentage of total number of colonies examined in $n_1(n_2)$ samples, where: $n_1$ is the total number of separate culture samples examined from bladder samples obtained from $n_2$ subjects. For cultures grown on fibronectin: Control: $n_1(n_2)$ =14(8); LT-2: $n_1(n_2)$=5(4); IC: $n_1(n_2)$=11(3). For cultures grown on collagen: Control: $n_1(n_2)$=18(13); LT2: $n_1(n_2)$=7 (6); IC: $n_1(n_2)$=13(6). Significance of changes in LT2-treated (or IC cultures), as compared to untreated control cultures were tested using Student's t test. *, P<0.001; P<0.05.

FIG. 2A: large arrowhead, superficial layer of urothelium; small arrowhead, basal layer of urothelium; FIG. 2B: large arrowhead, superficial layer of urothelium; small arrowhead, points to $\beta_1$ staining in the cell-cell contact areas of intermediate cells; arrow, points to intense $\beta_1$ staining in the basal layer of the urothelium (FIG. 2A, [bar, 30 µm]; FIG. 2B, [bar, 23 µm]).

FIG. 3 shows the distribution of CK8 and integrins in control, IC and LT-2 cultures. Control (FIGS. 3A, 3B, 3D and 3E) or IC cultures (FIGS. 3C,3F) were grown in complete F12* containing 0.2 mM $Ca^{2+}$ and 0.005% bovine pituitary extract. During their last 3 days in culture, all cell cultures grew in BPE-free, insulin-free F12* medium containing 0.2 mM $Ca^{2+}$. LT-2 cultures (FIGS. 3B, 3E) also received 25 µg/ml LT-2 during their last 3 days of growth in culture. The rest of control (FIGS. 3A, 3D) and IC cultures (FIGS. 3C, 3F) grew during their last 3 days in culture in the presence of the vehicle (0.5% ethanol), but no toxin. Cells were then fixed and probed with a monoclonal, affinity-purified primary antibody against CK8 (FIGS. 3A–3C), integrin subunit $\beta_1$ (FIGS. 3D,3F) or $\alpha_3$ (FIG. 3E). FIG. 3A, arrowhead, points to cells that display moderate, perinuclear CK8 expression; FIGS. 3B and 3C, bent arrow, points to highly CK8-expressing, loosely attaching cells at the border of the colony; straight arrow, points to highly CK8 expressing cells attaching on the top of the colony. FIG. 3D, arrowhead points to clusters of integrins. FIGS. 3E and 3F, arrowhead points to integrins lining the cell-cell contact area. (FIG. 3A, [bar, 65 µm]; FIG. 3B, [bar, 30 µm]; FIG. 3C, [bar, 45 µm]; FIG. 3D, [bar, 65 µm]; FIG. 3E, [bar, 30 µm]; FIG. 3F, [bar, 30 µm]).

FIG. 4 shows the distribution of low CK8 expressing and high CK8 expressing colonies in IC, control and LT-2 cultures. Cells grew on glass coverslips coated with 20 µg/ml collagen under conditions identical to those described in FIG. 1. Cells were probed with a monoclonal, affinity-purified antibody against CK8. A total of 100 randomly chosen colonies were examined and the number of cells in each colony was determined. For the analysis of results, colonies examined were divided in 10 groups as a function of the number of cells per colony, i.e. 1–10 cells per colony, respectively. The eleventh group consisted of all colonies containing more than 10 cells per colony. Colonies in each of the 11 groups were divided into two categories: low CK8 expressing (FIG. 4A) and high CK8 expressing, (FIG. 4B) the latter defined as a colony containing at lest one high CK8 expressing cell. Results are means ± standard deviation of colonies consisting of the respective number of cells per colony as a percentage of the total number of colonies examined in a total of $n_1$ cell samples from the bladders of $n_2$ patients. Control cultures: $n_1(n_2)$=6(5); LT-2 cultures: $n_1(n_2)$=3(3); IC cultures: $n_1(n_2)$=5(5). Significance of changes in LT-2(or IC cultures), as compared to untreated control were tested using Student's t test. *, P<0.001; P<0.05. control, open bar; LT-2, filled bar; IC, hatched bar.

FIG. 5 shows that integrins distribute to cell-cell contacts of all colonies consisting of more than 6 cells per colony. Cells grew on glass coverslips coated with 20 µg/ml collagen under conditions identical to those described in FIG. 1. Group A: Colonies consisting of 6 or more cells per colony as a percentage of all colonies examined in control (open bar), LT-2 (filled bar) and IC (hatched bar) cultures. Group B: Cells grown under conditions identical to those described in FIG. 1 were probed with a monoclonal, affinity-purified antibody against integrin subunit $\beta_1$. A total of 100 randomly chosen colonies in each type of culture were examined. Shown here are only colonies consisting of 6 or more cells per colony that display the integrin at cell-cell contact of at least two cells, as a percentage of all colonies examined in control (open bar), LT-2 (filled bar) and IC (hatched bar) cultures. Results are means ± standard deviation of the percentage of colonies measured in $n_1(n_2)$ samples, where $n_1$ is the total number of separate cell samples examined from bladder samples obtained from $n_2$ subjects. Control: $n_1(n_2)$=8(5); LT-2: $n_1(n_2)$=4(4); IC: $n_1(n_2)$ =5(5). Significance of changes in LT-2 (or IC) cultures, as compared to control were tested using Student's t test. *, P<0.001.

DETAILED DESCRIPTION OF THE INVENTION

The present invention compares proliferative and differentiation abilities and, the cellular distribution of integrins, in untreated basal urothelial cells isolated from patients with interstitial cystitis (IC) and control subjects (control), as well as basal urothelial cells from control subjects treated in vitro with lipoteichoic acid toxin from the gram-positive *Streptococcus faecalis* (LT-2).

The present invention is directed to a method of diagnosing interstitial cystitis in an individual, comprising the steps of: (i) obtaining primary cultures of urothelial cells from bladder biopsies of said individual; (ii) using primary cultures and a growth medium containing low levels of calcium and growth factors (i.e., growth conditions that simulate those in the basal layer of the urinary bladder by restricting proliferation and inhibiting terminal differentiation) to select urothelial cells of basal type and produe secondary cultures thereof; (iii) to measure colony size distribution in secondary cultures of basal urothelial cells by examining randomly chosen 100 colonies, determining the number of cells in each colony and dividing the colonies in 7 groups by criterion of number of cells per colony (1,2,3,4,5,6, or more than 6 cells per colony); (iv) to determine percentage of single cells and percentage of large colonies, i.e., the number of single cells and the number of colonies consisting of more than 6 cells per colony, respectively, as a percentage of all colonies examined in the secondary culture; (v) to compare percentage of single cells and percentage of large colonies to those in sample of similarly cultured urothelial cells taken from an individual not suspected of having interstitial cystitis.

The present invention is also directed to a method of diagnosing interstitial cystitis in an individual, comprising the steps of: (i) obtaining primary cultures of urothelial cells from bladder biopsies of said individual; (ii) using primary cultures and a growth medium containing low levels of calcium and growth factors to select urothelial cells of basal type and produce secondary cultures thereof; (iii) measuring proliferation using bromodeoxyuridine (BudU) incorporation and a immunocytochemical technique to detect it in cell nucei; (iv) to determine the percentage of single cells and large colonies that contain at least one BrdU-incorporating (i.e., proliferating) cell; (v) to determine the percentage of large colonies that contain 1,2,3,4,5, or more than 6 BrdU-incorporating cells; (vi) to compare percentage of single cells and large colonies that contain at least one BrdU-incorporating cell, and, the percentage of large colonies that contain 1,2,3,4,5, or more than 6 BrdU-incorporating cells, to that in a sample of similarly cultured urothelial cells taken from an individual not suspected of having interstitial cystitis.

The present invention is further directed to a method of diagnosing interstitial cystitis in an individual, comprising the steps of: (i) obtaining primary cultures of urothelial cells from bladder biopsies of said individual; (ii) using primary cultures and a growth medium containing low levels of calcium and growth factors to select urothelial cells of basal type and produce secondary cultures thereof; (iii) measuring differentiation and detecting it by an immunofluorescence microscopy technique; (iv) to determine the percentage of single cells and the percentage of large colonies that contain at least one intense cytokeratin 8-expressing (i.e., differentiated) cell; (v) to determine the percentage of large colonies that contain 1,2,3,4,5, or more than 6 intense cytokeratin 8-expressing cells; (vi) to compare percentage of single cells and the percentage of large colonies that contain 1,2,3,4,5, or more than 6 intense cytokeratin 8-expressing cells to that in a sample of similarly cultured curothelial cells taken from an individual not suspected of having interstitial cystitis.

The present invention is also directed to a method of diagnosing interstitial cystitis in an individual, comprising the steps of: (i) obtaining primary cultures of urothelial cells from bladder biopsies of said individual; (ii) using primary cultures and a growth medium containing low levels of calcium and growth factors to select urothelial cells of basal type and produce secondary cultures thereof; (iii) measuring differentiation by probing cells with antibodies against integrins and examining its presence at cell-cell contacts; (iv) to determine the percentage of large colonies that express integrins at cell-cell contacts of 2,3,4,5,6, or more than 6 cells; (v) to compare percentage of large colonies that express integrins at cell-cell contacts of 2,3,4,5,6, or more than 6 cells to that in a sample of similarly cultured urothelial cells taken from an individual not suspected of having interstitial cystitis.

The present invention is also directed to a method of diagnosing interstitial cystitis in an individual, comprising the steps of: (i) obtaining primary cultures of urothelial cells from bladder biopsies of said individual; (ii) using primary cultures and a growth medium containing low levels of calcium and growth factors to select urothelial cells of basal type and produce secondary cultures thereof; (iii) measuring differentiation by probing cells with antibodies against cadherins and catenins, proteins that distribute to cell-cell contacts of differentiated epithelial cells and are crucial for normal cell-cell interactions and to examine their presence at cell-cell contacts; (iv) to determine the percentage of large colonies that express cadherins (and catenins) at cell-cell contacts of 2,3,4,5,6, or more than 6 cells; (v) to compare percentage of large colonies that express cadherins (and catenins) at cell-cell contacts of 2,3,4,5,6, or more than 6 cells to that in a sample of similarly cultured urothelial cells taken from an individual not suspected of having interstitial cystitis.

The present invention is directed to a method of diagnosing interstitial cystitis in an individual, comprising the steps of: (i) obtaining primary cultures of urothelial cells from bladder biopsies of said individual; (ii) using primary cultures and a growth medium containing low levels of calcium and growth factors to select urothelial cells of basal type and produce secondary cultures thereof; (iii) probing cells with antibodies against phosphotyrosine and nitrotyrosine; (iv) to determine the percentage of large colonies that express phosphotyrosine and nitrotyrosine at cell-cell contact of 2,3,4,5,6, or more than 6 cells; (v) to compare percentage of large colonies that express phosphotyrosine and nitrotyrosine at cell-cell contacts of 2,3,4,5,6, or more than 6 cells to that in a sample of similarly cultured urothelial cells taken from an individual not suspected of having interstitial cystitis.

Finally, the present invention is also directed to a method of diagnosing interstitial cystitis in an individual, comprising the steps of: obtaining primary cultures of urothelial cells from bladder biopsies of said individual; using primary cultures and a growth medium containing low levels of calcium and growth factors to select urothelial cells of basal type and produce secondary cultures thereof; measuring the percentage of apoptotic cells in the entire culture; measuring the percentage of large colonies that contain 1,2,3,4,5,6, or more than 6 apoptotic cells; and comparing the percentage of said colonies to baseline values of the same parameters determined in samples of similarly cultured urothelial cells taken from individuals not suspected of having interstitial cystitis.

The following examples are given for the purpose of illustrating various embodiments of the invention and are not meant to limit the present invention in any fashion.

EXAMPLE 1
Interstitial cystitis and control patients

Bladder biopsies were obtained for diagnostic purposes from 13 control patients (stress incontinence) and 6 patients with interstitial cystitis. The mean age of patients was 50±19 patients (range 24 to 72 years) in the control group and 38±4 (range 35 to 40 years) in the interstitial cystitis group of patients. The diagnosis of interstitial cystitis was established by standard NIH criteria[44]. Biopsies from the dome of the urinary bladder, and the right and left lateral walls were collected utilizing a Storz rigid cup biopsy forceps.

EXAMPLE 2
Urothelial cell culture

Epithelial cells were isolated from pieces of bladder biopsies as previously described[8-10,38,53]. Briefly, Ham's F12 growth medium supplemented with 0.1 mM nonessential amino acids, 2 mM glutamine (GIBCO, Grand Island, N.Y.), 1 µg/ml hydrocortisone (MERCK, SHARPE AND DOHME, Pointe Claire, Canada), 5 µg/ml transferrin, 2.7 mg/ml dextrose, and 10 µg/ml insulin (all from SIGMA, St. Louis. Mo.) was designated medium F12*. Primary cultures grew in F12* medium supplemented with 1% fetal bovine serum (FBS) (GIBCO, Grand Island, N.Y.). Secondary cultures used in the present studies grew in complete serum-free F12* medium, containing in addition to F12*, 0.005% bovine pituitary extract (BPE).

EXAMPLE 3
Immunofluorscence microscopy studies

Biopsy bladder tissue specimens were prepared for immunohistochemistry as previously described[14]. Briefly, specimens were fixed at 4° C. overnight in an acid-alcohol solution containing 96% ethanol, 1% glacial acetic acid and 3% distilled water and then paraffin-embedded using standard procedures. Paraffin-embedded tissue sections were de-paraffinized immediately before staining as described by Folkword et al.[14] and then subjected to treatment with 1M NaCl for 3 days at 4° C.

Cell cultures were prepared for immunofluorescence microscopy as previously described[10,55]. Briefly, cells grown on cover slips coated with fibronectin or collagen (20 µg/ml) were washed once with warm (37° C.) phosphate buffered saline (PBS) and fixed with 3.5% paraformaldehyde (20 minutes, room temperature (RT)). After quenching free aldehyde groups with 0.1M NH$_4$Cl in PBS (15 minutes, RT), cells were washed once with PBS (15 minutes, RT). Cells were then permeabilized by incubating with 0.1% Triton X-100 (10 minutes, RT) and washed three times with PBS (5 minutes each, RT).

Treated cell cultures and tissue sections were incubated with 1% BSA (in PBS, 37° C., 30 minutes) to block non-specific sites, followed by treatment with primary antibody (45 minutes, 37° C.). Finally, samples were washed three times with PBS (15 minutes each, RT), followed by treatment with secondary antibody conjugated to fluorescein (45 minutes, 37° C.). No label was seen in control samples treated with secondary antibody alone. Cells were mounted, viewed with a NIKON OPTIPHOT fluorescence microscope (Garden City, N.Y.) and photographed with Ilford HP5 film (Basildon, UK).

EXAMPLE 4
Materials

Lipoteichoic acid ([LT-2], from *Streptococcus faecalis*) was purchased from SIGMA. Fibronectin (fibronectin) was from SIGMA (St. Louis, Mo.) and type I collagen (CO) was purchased from CELTRIX LABORATORIES (Santa Clara, Calif.). Primary antibodies against integrin subunit $\beta_1$ and $\alpha_3$ were purchased from CHEMICON (Temecula, Calif.) and GIBCO (Grand Island, N.Y.), respectively. Primary antibody against cytokeratin 8 was from AMAC, INC (Westbrook, Me.). Secondary antibodies (affinity-purified fluorescein isothiocyanate (FITC)-conjugated goat anti-mouse IgG) were purchased from CAPPEL (Durham, N.C.).

EXAMPLE 5
Cultured uroepithelial cells are distributed in colonies

Figure 1:
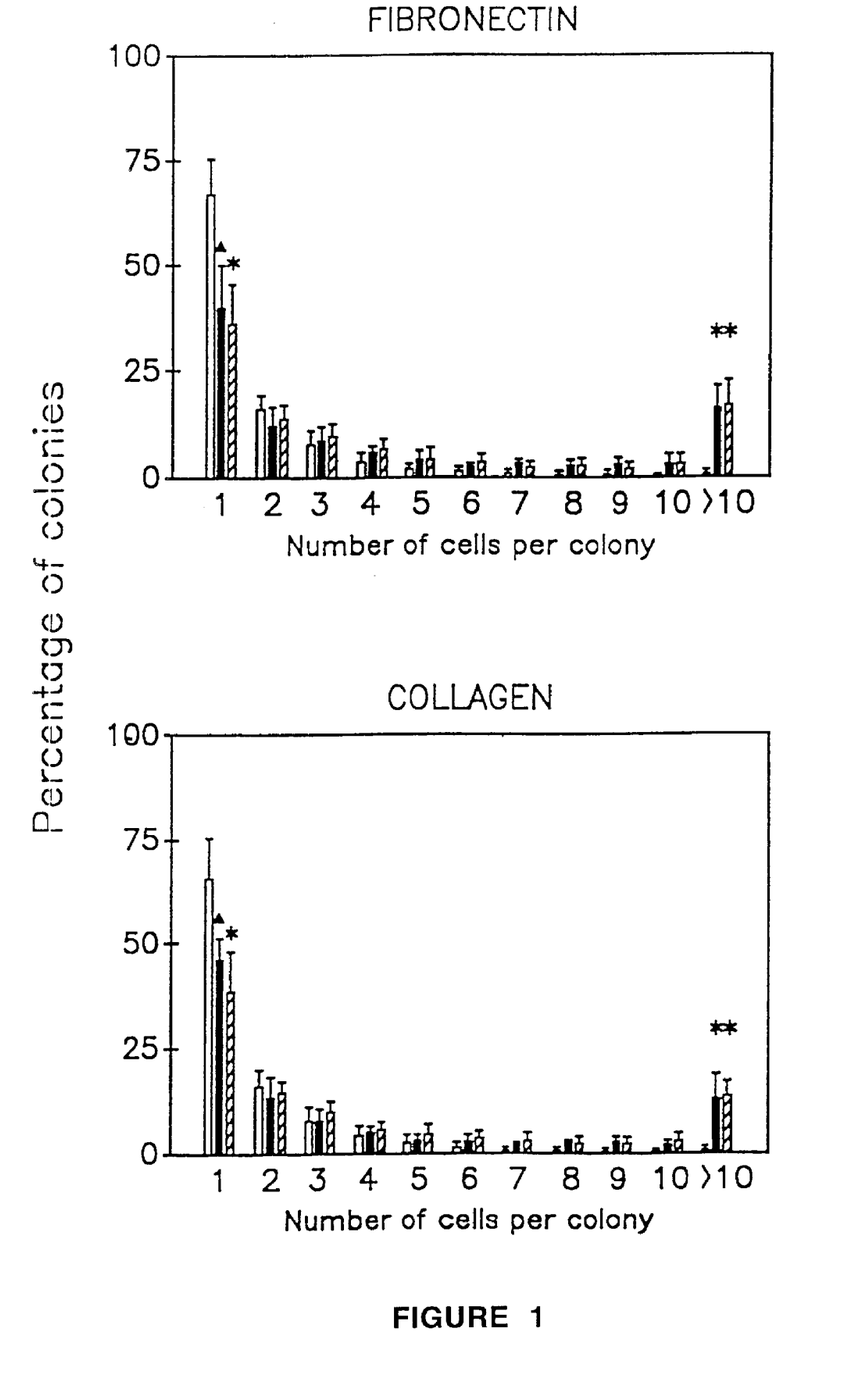

Studies were carried out in secondary cultures (first passage) of cells isolated from the urinary bladder of interstitial cystitis patients and control subjects. Cells were grown on glass cover slips coated with 20 µg/ml fibronectin (FN) or collagen (CO), in a low $Ca^{2+}$ (0.2 mM) low bovine pituitary extract (0.005%) growth medium. Examination of cultures grown under these conditions revealed that they consisted of colonies with varying number of cells per colony. To evaluate the distribution of cells into colonies of varying size, a total of randomly chosen 100 colonies were first examined in untreated control cultures grown on fibronectin or collagen. The number of cells in each colony was determined. For the analysis of results, colonies examined were divided into ten groups as a function of the number of cells per colony, i.e., 1–10 cells per colony, respectively. The eleventh group consisted of all colonies containing more than 10 cells per colony. This was necessary because stratification often occurred in large colonies and cell numbers could not be accurately determined. Results in FIG. 1 show that the distribution of cells in colonies of varying size was very reproducible, similar in cultures grown on fibronectin (FIG. 1A) or collagen (FIG. 1B). The percentage of colonies (i.e. the number of colonies in a group as a percentage of the total number of colonies examined), decreased gradually as a function of the number of cells per colony in control cultures (FIG. 1).

EXAMPLE 6
Colony distribution in LT-2 and IC cultures compared to control cultures Some control cultures were treated during their last 3 days in culture with 25 µg/ml lipoteichoic acid from the gram-positive *Strep. faecalis* (LT-2). The concentration of LT-2 used for treatments was chosen based on earlier dose-response studies in urothelial cells. In those studies, LT-2 stimulated uroepithelial proliferation in a dose-dependent manner, with maximal effect observed at 50 µg/ml[53], suggesting that LT-2 effects were not the result of induction of general toxicity. IC cultures were exposed during their last 3 days in culture to the vehicle (ethanol), to maintain the level of ethanol constant in all samples at 0.5% (v/v). Some of the control cultures were exposed to vehicle alone during their last three days in culture (control samples).

The population of IC large colonies (consisting of 6 or more cells per colony) increased in cultures grown on fibronectin (FIG. 1A, hatched bar) and collagen (FIG. 1B, hatched bar) as compared to that in untreated control (FIG. 1, open bar). A comparable increase occurred in the population of large colonies (consisting of 6 or more cells per colony) in LT-2 cultures (FIG. 1, filled bar). The significant decrease observed in the population of single IC and single LT-2, as compared with single control cells was comparable to the increase in large colonies in the respective experimental groups. This is consistent with the possibility that the increase in the population of large colonies is due to the stimulation of a subpopulation of single cells to proliferate in LT-2 as compared to control groups. The changes in IC may be due to earlier exposure to injection, in vivo, of basal IC cells with high proliferative potential.

EXAMPLE 7
State of differentiation in LT-2 and IC cultures compared to controls To examine the state of differentiation of untreated control, LT-2 and IC cultures, cells were probed with a monoclonal, affinity-purified antibody against cytokeratin 8

(CK8). Using antibodies against CK8, all epithelial cells in the transitional epithelium of the human bladder have been shown to express this protein. However, superficial, terminally differentiated cells ("umbrella cells") were strongly positive, whereas poorly differentiated basal and intermediate cells were only moderately reactive[30,41]. This has been corroborated in sections from control human bladders that have been probed for CK8, in which intense staining in the superficial layer (FIG. 2A, large arrowhead), but only moderate staining in the underlying layers of the uroepithelium (FIG. 2A, small arrowhead) was observed. Based on this pattern of CK8 expression in intact tissue, cultured cells displaying moderate CK8 distribution were defined "poorly differentiated", whereas cells displaying high CK8 expression were defined "more differentiated".

Figure 3:
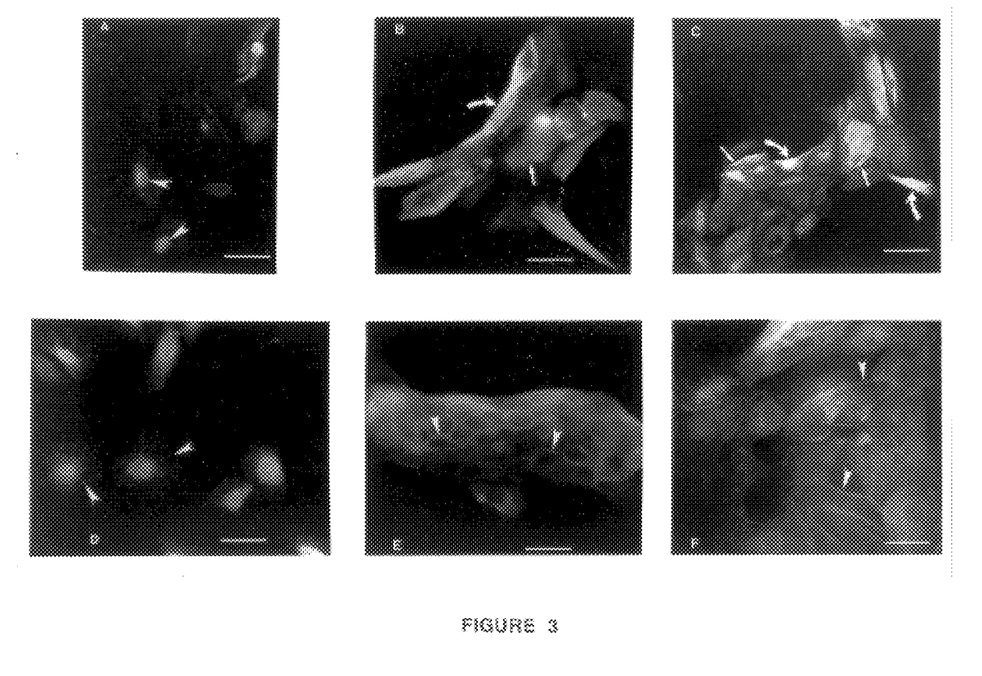

An example of poorly differentiated untreated control cells, displaying mostly perinuclear CK8, is shown in FIG. 3A (arrowhead). In contrast, large colonies of LT-2 and IC cultures grown under identical conditions displayed fibers or intense staining of CK8 on the entire surface of cells loosely attaching at the border of the colony (FIGS. 3B, 3C, bent arrows) or in cells attaching on the top of the colony (FIGS. 3B, 3C, straight arrow), indicating that these colonies contained terminally differentiated cells.

To evaluate the state of differentiation in the entire population of cultured cells, a total of randomly chosen 100 colonies probed with the antibody against CK8 were examined in control, LT-2 or IC cultures. CK8 expression was similar in cells grown on fibronectin or collagen. Only results obtained in cultures grown on collagen are given below.

Some of the colonies consisting of 5 or less cells per colony displayed only low CK8-expressing cells (i.e. were poorly differentiated) (FIG. 4A), whereas some of these colonies contained high CK8-expressing, terminally differentiated cells (FIG. 4B). The percentage of high CK8-expressing, more differentiated colonies consisting of 5 or less cells per colony was similar in control (FIG. 4B, open bar), LT-2 (FIG. 4B filled bar) or IC cultures (FIG. 4B, hatched bar). In contrast, the subpopulation of low CK8-expressing colonies consisting of 5 or less cells per colony was lower in LT-2 and IC cultures as compared to control cultures (FIG. 4A). This was especially evident in a subpopulation of low CK8-expressing, poorly differentiated, LT-2 -treated (FIG. 4A, filled bar) and IC (FIG. 4A, hatched bar) single cells which were half of the subpopulation of poorly differentiated single cells in control cultures (FIG. 4A, open bar).

Low CK8-expressing colonies consisting of 6 or more cells per colony represented a negligible percentage of the entire population examined under all experimental conditions (FIG. 4A), suggesting that no poorly differentiated colonies were present in this group. Most of the subpopulation of colonies consisting of 6 or more cells per colony contained high CK8-expressing cells, indicating that they were well differentiated (FIG. 4B). The subpopulation of high CK8-expressing colonies consisting of 6 or more cells per colony, especially large colonies of more than 10 cells per colony, increased several fold in IC and LT-2 cultures, as compared to control cultures (FIG. 4B).

EXAMPLE 8

Figure 2:
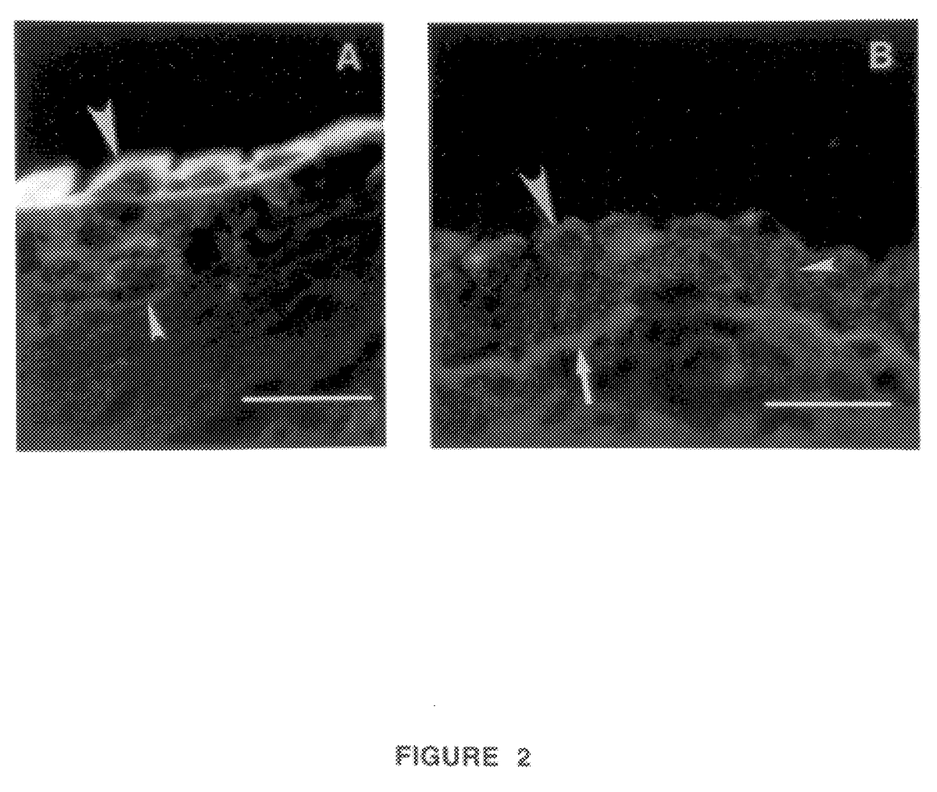
FIG. 2 shows the distribution of cytokeratin 8 (CK8) and $\beta_1$ subunit-containing integrins in the bladder urothelium from control subjects. Bladder biopsy specimens from control subjects were prepared for immunofluorescence as described below. Tissue sections were immunohistochemically stained for CK8 (FIG. 2A) or $\beta$1 (FIG. 2B).

Well differentiated LT-2 and IC colonies, consisting of 6 or more cells per colony, display integrins at cell-cell contacts Earlier studies in skin keratinocytes had shown a coupling between the state of epithelial differentiation and $\beta_1$ subunit-containing integrin (e.g. $\alpha_3\beta_1$) expression[21]. Similarly to the skin epithelium, a $\beta_1$ subunit-containing integrin whose presence was recently reported in the urothelium, $\alpha_3\beta_1$[10,24] was prominently expressed in the basal layer of poorly differentiated basal urothelial cells, abutting the basement membrane in bladder sections (FIG. 2B, large arrowhead). $\beta_1$ integrins were moderately expressed at cell-cell contact areas in intermediate layers of the urothelium (FIG. 2B, small arrowhead). Based on this distribution of $\beta_1$ in bladder tissue, it was postulated that as control cells differentiate in culture, $\beta_1$ subunit-containing integrins (e.g. $\alpha_3\beta_1$) will redistribute from structures allowing tight interactions with the basement membrane to cell-cell contact areas. It was also postulated that since a dramatic increase in a subpopulation of differentiated colonies by criterion of high CK8 expression was evident in IC and LT-2 cultures (FIG. 4), a similar increase should be seen in a population of colonies consisting of 6 or more cells per colony that express $\beta_1$ integrins at cell-cell contacts.

To examine these possibilities, cell cultures were probed with monoclonal, affinity purified antibodies against integrin subunits $\alpha_3$ and $\beta_1$. An example of single cell and 2-cell colonies of control cultures is shown in FIG. 3D. As expected for poorly differentiated small colonies that attach firmly to the substrate[10], the integrin was distributed in clusters (FIG. 3D, arrowhead). In contrast, the integrin localized to cell-cell contacts in large colonies prevalent in LT-2 (FIG. 3E, arrowhead) or IC cultures (FIG. 3F, arrowhead).

Figure 4:
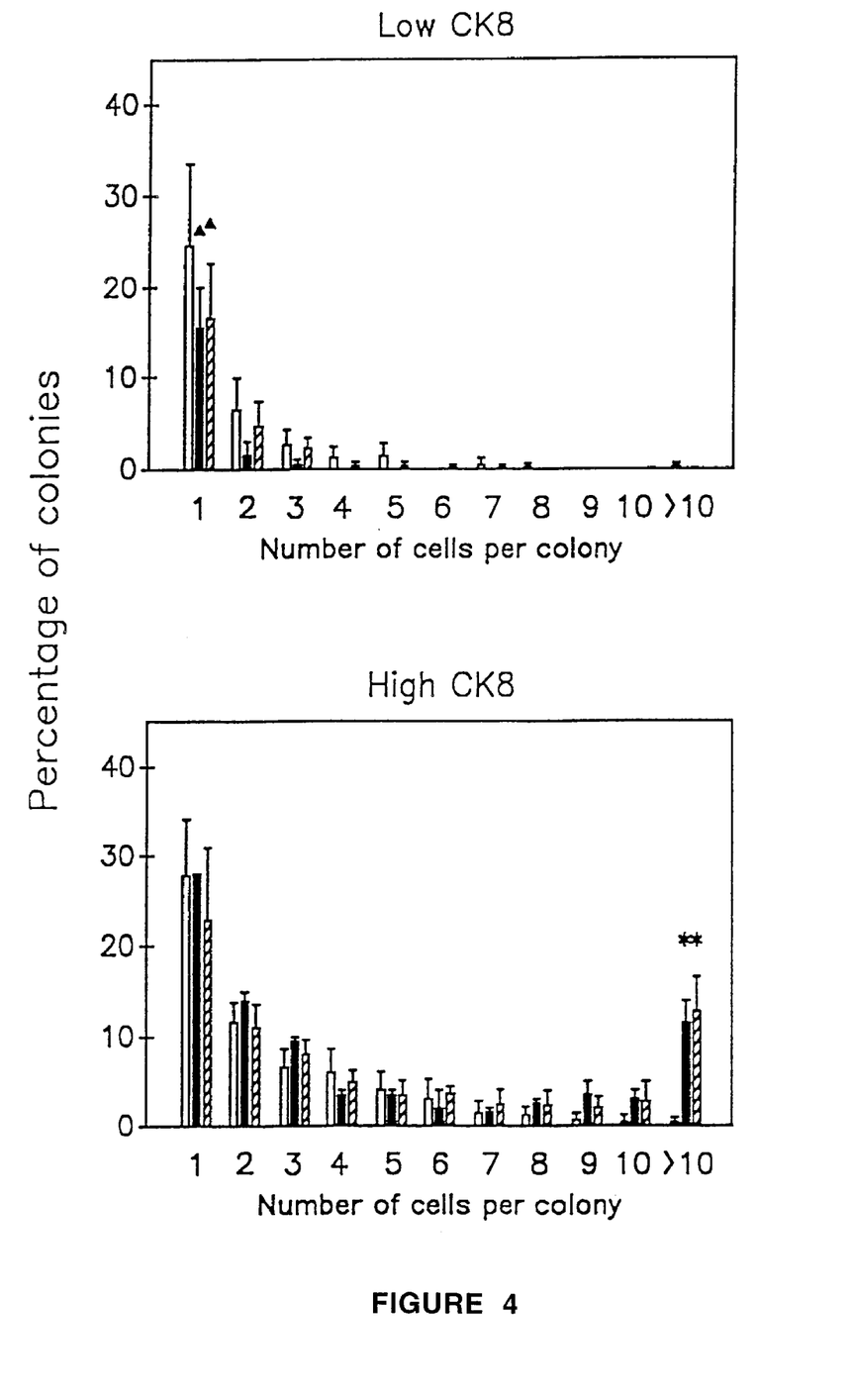
Figure 5:
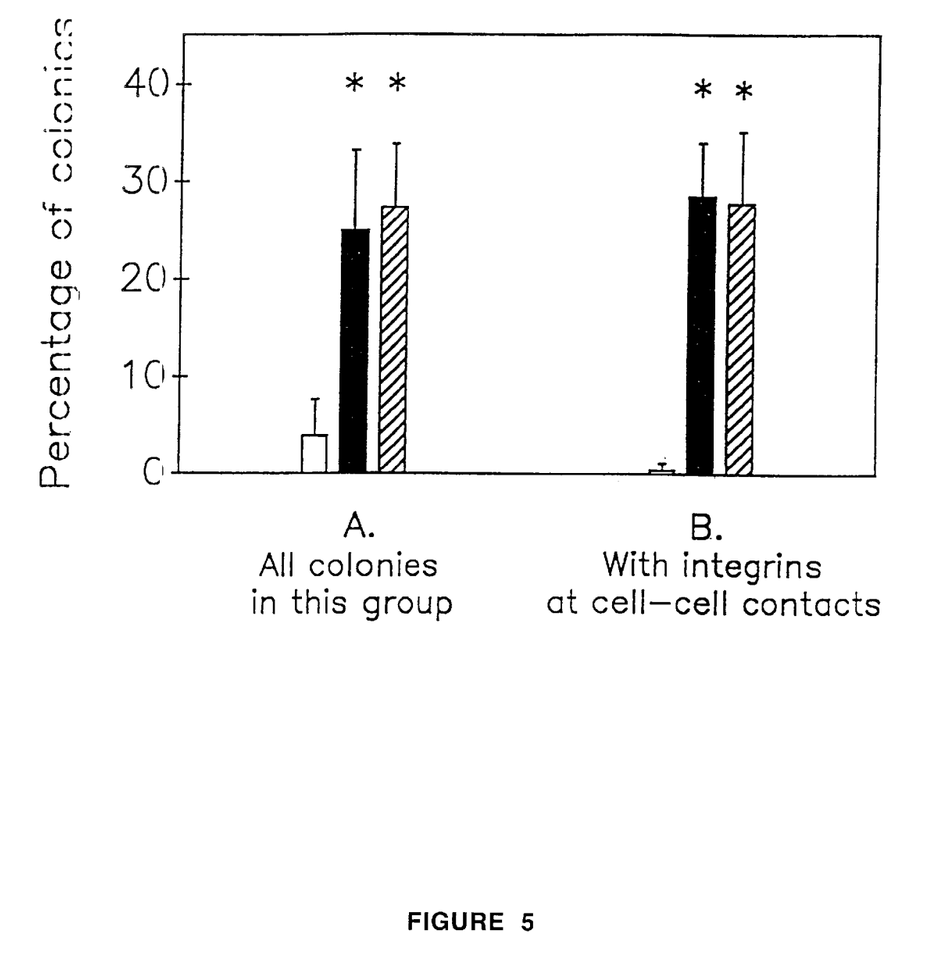

That integrins had distributed to cell-cell contacts in the entire subpopulation of well differentiated colonies consisting of 6 or more cells per colony was tested next. A total of randomly chosen 100 colonies probed with antibodies against $\alpha_3$ or $\beta_1$ were examined as described above. Analysis focused on the population of large colonies (>6 cells per colony), because this entire subpopulation had been shown to be well differentiated by criterion of high cytokeratin 8 expression (FIG. 4). The percentage that this subpopulation represented in the entire population of colonies (FIG. 5, left group of data) was compared with the percentage of colonies consisting of 6 or more cells that expressed integrins at cell-cell contacts (FIG. 5, right group of data). Under all conditions tested, the size of the subpopulation of colonies consisting of 6 or more cells per colony was identical to the size of the subpopulation of colonies consisting of 6 or more cells per colony that expressed integrin at cell-cell contacts. This subpopulation of colonies was many fold larger in LT-2 and IC cultures as compared to untreated control cultures.

Urothelial detachments and mucosal splittings are histopathological findings typical to the interstitial cystitis bladder[20,27,40]. They suggest that the architecture of the urothelium is altered in this disease. Processes involved in the maintenance of urothelial architecture are not completely clear. In contrast, a great deal is known about such processes in the skin[21,31,47,48]. Normal skin architecture depends on a balance between: (i) renewal by proliferation confined to a small population of cells in the basal layer; (ii) differentiation and death, processes that involve changes in levels and cellular distribution of integrin receptors for extracellular matrix, resulting in detachment of cells from the basal layer and their move upwards through the suprabasal layers[21,31,47,48,39]. It has been postulated that interstitial cystitis may be caused by abnormalities in one or both of these processes, induced by exposure of basal uroepithelial cells to bacterial toxins accumulating at foci of infection. The present studies focused on lipoteichoic acids, cell wall components of gram positive bacteris, for the following reasons: (1) Gram positive bacteria (e.g., enterococci), are recognized as pathogens in urinary tract infections[50,57]; (ii) Attachment to epithelial cells, including epithelial cells in the urinary tract, enhances the ability of lipoteichoic acids produced by these bacteria, to trigger mucosal inflammation[58]; (iii) Under experimental conditions, lipoteichoic acids migrate to areas considerably remote from their area of infection[59] and accumulate in tissues where they are likely to induce pathogenesis[19]; (iv) Repeated administration of LT in vivo has been shown to cause gross morphological changes in the basement membrane of the urothelium and cells in the basal layer of the urothelium[59]. (v) Lipoteichoic acids have been previously shown to induce the proliferation of hematopoietic and lymphatic cells[60], as well as thymocytes[61]. Based on these studies, as well as earlier studies carried out in urothelial cells[53], it was postulated that exposure to stem cells in the basal layer of the urothelium to lipoteichoic acids during suburothelial or systemic infection may alter the proliferative ability of these cells, inducing the IC phenotype. The present invention examined in vitro: (i) untreated urothelial cells isolated from patients with interstitial cystitis (IC); (ii) untreated urothelial cells isolated from control subjects (control); and (iii) urothelial cells from control patients treated in vitro with lipoteichoic acid toxin from the gram-positive *Streptococcus faecalis* (LT-2). To simulate conditions in the basal layer of the normal urothelium that do not support terminal differentiation, cell cultures were grown on a collagen-coated or fibronectin-coated substrate, in low $Ca^{2+}$, low bovine pituitary extract medium. Studies in vitro have shown that epithelial differentiation is inhibited in low $Ca^{2+}$ medium[54].

Isolated secondary cultures of cells from control displayed a highly reproducible colony size distribution. The heterogeneity and reproducibility of the proliferative ability of isolated control urothelial bladders was not surprising. Earlier in vivo studies in skin had shown that proliferation in that multilayer epithelium was largely confined to the basal layer abutting the basement membrane[48] and evidence exists for heterogeneity within this proliferative compartment[22]. Within the population of basal skin keratinocytes with proliferative ability, a limited number of dividing cells with high proliferative potential are believed to correspond to stem cells. Cells with intermediate proliferative ability have been named transit amplifying cells[35]. The majority of skin keratinocytes isolated and grown in vitro "remember" what they were in vivo[49]. In analogy with the skin, the subpopulation of basal uroepithelial cells with high proliferative ability, possibly stem cells, was expected to be very small in the normal bladder urothelium. Indeed, the progeny of such highly proliferating cells, colonies consisting of more than 10 cells per colony represented a small percentage of the colonies in cultures from control patients grown on fibronectin (FIG. 1A) or collagen (FIG. 1B). The majority of colonies consisted of 1–5 cells per colony (FIG. 1) and a considerable part of them were poorly differentiated cultures from control patients (FIG. 4). The percentage of large colonies (defined as those consisting of 6 or more cells per colony) was low in untreated control cultures (FIG. 1) and these colonies were well differentiated (FIG. 4). These in vitro data are consistent with the possibility that most of the progenitors of colonies growing in the cultures, cells residing in the normal basal layer, had limited proliferative ability and were probably transit amplifying cells.

In contrast to untreated control cultures, a dramatic increase was found in the percentage of large colonies from interstitial cystitis patients (IC) although they grew under identical restricting condictions (FIG. 1). Large IC colonies (6 cells/colony) were well differentiated (FIG. 4) and all expressed $\beta_1$ integrins at cell-cell contacts (FIGS. 3F, FIG. 5) rather than in clusters more typical of poorly differentiated cultures from control patients (FIG. 3D). Moreover, a decrease was found in the percentage of poorly differentiated single IC cells as compared to percentage of single control cells (FIGS. 1A, 4A, hatched bars). Thus, a subpopulation of single cells in the basal layer of the interstitial cystitis urothelium may have acquired increased ability to proliferate and differentiate under conditions that do not favor these processes in the normal urothelium. Redistribution of $\beta_1$ in such colonies from structures allowing interaction of the basal cells with the basement membrane to cell-cell contacts, could be the cause for urothelial detachments typical to the interstitial cystitis bladder[20,27,40]. In contrast to transformed cells, the proliferative ability of toxin-exposed basal cells may be limited, ending in terminal differentiation. This may lead to focal depletion of the store of basal cells with potential proliferative ability at sites of infection and may explain ulcers developing in older patients with interstitial cystitis[20,27].

Interestingly, when compared with untreated control cultures, changes almost identical to those measured in IC cultures were found in cultures of uroepithelial cells isolated from control bladders, but treated in vitro with the bacterial toxin LT-2. Thus, a comparable decrease was found in a subpopulation of poorly differentiated single cells (FIG. 1A, FIG. 4A, filled bars) and an increase was found in the percentage of large colonies (FIG. 1). Like IC cultures, all LT-2 large colonies (6 cells/colony) were well differentiated (FIG. 4) and all expressed $\beta_1$ at cell-cell contacts (FIG. 3E, FIG. 5). These data are consistent with changes prevailing in the isolated IC cultures and may have been caused in vivo by exposure of epithelial cells in the basal layer of the urothelium to bacterial toxins (e.g. LT-2).

In conclusion, these studies suggest that high LT-2 concentrations developing at foci of infection may affect proliferative and differentiation abilities of a subpopulation of basal uroepithelial cells with high proliferative potential. Redistribution of $\beta_1$ integrins at foci of differentiation in the basal layer of the interstitial cystitis urothelium, from structures allowing interaction with the basement membrane to cell-cell contacts, could be the cause for urothelial detachments typical to the interstitial cystitis bladder. The presence of basal cells with toxin-induced, more differentiated phenotype, in the basal layer provides a cellular mechanism that could explain the production of autoantibodies in patients with interstitial cystitis[26] and a putative pathway for the stimulation of an autoimmune response[37].

The following references were cited herein.
1. Albelda, S. M., et al., *FASEB J.*, 4:2868–2880, (1990).
2. Anderson J. B., et al., *Br. J. Urol.*, 63:58–62, (1989).
3. Aronson M., et al., *Infect. Immun.*, 56:1615–1617, (1988).
4. Carter, W. G., et al., *J. Cell Biol.*, 110:1387–1404, (1990).
5. Dedhar, S., et al., *J. Cell Biol.*, 104:585–593, (1987).
6. De Man P., et al., *Infect. Immun.*, 57:3383–3388, (1989).
7. De Vuono, J., et al., *Infect. Immun.*, 72:255–256, (1978).
8. Elgavish, A., *Infect. Immun.*, 61:3304–3312, (1993).
9. Elgavish, A., et al., *Amer. J. Physiol.*, 261:C916–C926, (1991).
10. Elgavish, A., et al., *Amer. J. Physiol.*, 266:C1552-C1559, (1994).
11. Elliott, T. S. J., et al., *J. Infect.*, 11:191–199, (1985).
12. Fall, M., et al., *J. Urol.*, 133:771–773, (1985).
13. Figdor, C. G., et al.,: Regulation of cell adhesion. In: *Adhesion: Its role in Inflammatory Disease*. Edited by J. M. Harlan and D. Y. Liu. New York: Freeman, pp. 151–182, (1992).
14. Folkvord, J. M., et al., *J. Histochem. Cytochem.*, 37:105–113, (1989).

15. Hedelin, H. H., et al., *Sexually Transmit. Dis.*, 10:327, (1983).
16. Hynes, R. O., *Cell*, 48:549–554, (1987).
17. Hynes, R. O., *Cell*, 69:11–25, (1992).
18. Hynes, R. O., et al., *Cell*, 68:303–322, (1992).
19. Hyzy, J., et al., *Microbial Pathogenesis*, 13:123–132, (1992).
20. Johansson, S. L., et al., *J. Urol.*, 143:1118–1124, (1990).
21. Jones, P. H., et al., *Cell*, 73:713–724, (1933).
22. Juliano, R. L., *Biochim. Biophys. Acta*, 907:261–268, (1987).
23. Larjava, H., et al., *J. Cell Biol.*, 110:803–815, (1990).
24. Liebert, M., et al., *Amer. J. Pathol.*, 144:1016–1022, (1994).
25. Linder, H., et al., *Infect. Immun.*, 56:1309–1313, (1988).
26. Matilla, J., et al., *Clin. Immun. Immunopathol.*, 32:81–89, (1984).
27. Messing, E. M.: Interstitial cystitis and related syndromes. In: *Urology*. Edited by Campbell, M., ch. 24, pp. 1070–1087, (1986).
28. Moldwin, R. M., et al., *J. Urol.*, 147:285, (1992).
29. Moldwin, R. M., et al., *J. Urol.*, 148:154–157, (1992).
30. Moll, R., et al., *Amer. J. Path.*, 132:123–144, (1988).
31. Nicholson, L. J., et al., *J. Cell Sci.*, 98:225–232, (1991).
32. Ohshima, Y., et al., *Int. J. Med. Microbiol.*, 277:357–363, (1992).
33. Parsons, C. L., et al., *J. Urol.*, 145:732–735, (1991).
34. Parsons, C. L., et al., *Science* 208:605–607, (1980).
35. Pauli, B. U., and Weinstein, S.: Rat bladder carcinomas: a model system in vivo and in vitro. In: *In vitro models for cancer research*. Edited by M. M. Weber. Boca Raton, Fla.: CRC Press, pp. 169–200, (1986).
36. Potten C. S., et al., *J. Cell Sci.* (Suppl.) 10:45–62, (1988).
37. Ratliff, T. L., et al., *Urologic Clinics of North Amer*, 21:21–30, (1994).
38. Reznikoff, C. A., Swaminathan, S., and Verma, A. K.: Cultured normal human urothelial cells: A new system for in vitro carcinogenesis studies. In: *In vitro models for Cancer Research*, Edited by M. Weber and L. Sikeley. Boca Raton, Fla.: CRC Press. pp. 63–101, (1986).
39. Ruoslahti, E., et al., *Cell* , 77:477–478, (1994).
40. Said, J. W., et al., *Modern Pathol.*, 2:593–602, (1988).
41. Schaafsma, H. E., et al., *Histochem.*, 91:151–159, (1989).
42. Schwartz, M. A., et al., *Proc. Natl. Acad. Sci.*USA, 88:7849–7853, (1991).
43. Shahin, R. D., et al., *J. Immunol.*, 138:3475–3480, (1987).
44. Striker, G. E., *J. Urol.*, 142:139, (1988).
45. Svanborg Eden, C., et al., *Biochem. Soc. Transact.*, 17:464–466, (1989).
46. Warren, J. W., *Urologic Clinics of North America*, 21:31–39, (1994).
47. Watt, F., *J. Cell Biol.*, 98:16–21, (1984).
48. Watt, F. M., *Curr. Opin. Cell Biol.*, 1:1107–1115, (1989).
49. Watt, F. M., et al., *J. Cell Sci.*, 99:397–405, (1991).
50. Wells, C. L., et al., *J. Infect. Dis.*, 162:82–90, (1990).
51. Werb, Z., et al., *J. Cell Biol.* 109:877–889, (1989).
52. Wicken, A. J., et al., *Biochim. Biophys. Acta*, 604:1–26, (1980).
53. Wille, J. J., et al., *J. Cell. Physiol.*, 150:52–58, (1992).
54. Wille, J. J., et al., *J. Cell. Physiol.* 121: 1–44, (1984).
55. Woods, A., et al., *Mol. Biol. Cell* 5:183–192, (1994).
56. Yamada, K. M., et al., *Cancer Res.* 50:4485–4496, (1990).
57. Hirose, T., et al., *Urol. Res.* 17:125–129, (1989).
58. Beachey, E. H., et al., *Respiration* 55 (suppl 1):33–40, (1989).
59. Leon, O., et al., *Can. J. Microbiol.* 33:709–717, (1987).
60. Ohshima, Y., et al., *Int. J. Med. Microbiol.* 276:86–93, (1991).
61. Ohshima, Y., et al., *Int. J. Med. Microbiol.* 277:357–363, (1992).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of diagnosing interstitial cystitits in an individual, comprising the steps of:

obtaining primary cultures of urothelial cells from bladder biopsies of said individual;

using primary cultures and a growth medium containing low levels of calcium and growth factors to select urothelial cells of basal type and produce secondary cultures thereof;

measuring colony size distribution in secondary cultures of basal urothelial cells by examining randomly chosen 100 colonies, determining the number of cells in each colony and dividing the colonies in 7 groups according to the number of cells per colony;

determining the number of single cells and the number of large colonies as a percentage of all colonies examined in the secondary culture;

comparing percentage of single cells and percentage of large colonies to those in a sample of similarly cultured urothelial cells taken from an individual not suspected of having interstitial cystitis.

2. The method of claim 1, wherein the calcium in the medium has a concentration of about 0.2 mM.

3. The method of claim 1, wherein said medium contains 0.005% bovine pituitary extract (BPE).

4. The method of claim 1, wherein cells are grown on glass slides coated with matrix protein.

5. A method of diagnosing interstitial cystitits in an individual, comprising the steps of:

obtaining primary cultures of uroepithelial cells from bladder biopsies of said individual;

using primary cultures and a growth medium containing low levels of calcium and growth factors to select urothelial cells of basal type and produce secondary cultures thereof;

measuring proliferation using bromodeoxyuridine (BrdU) incorporation and a immunocytochemical technique to detect it in cell nuclei;

determining the percentage of single cells that incorporate BrdU;

determining the percentage of large colonies that contain more than 6 BrdU-incorporating cells; and comparing percentage of single cells that incorporate BrdU and the percentage of large colonies that contain more than 6 BrdU-incorporating cells to that in a sample of similarly cultured urothelial cells taken from an individual not suspected of having interstitial cystitis.

6. The method of claim 5, wherein the calcium in the medium has a concentration of about 0.2 mM.

7. The method of claim 5, wherein said medium contains 0.005% bovine pituitary extract (BPE).

8. The method of claim 5, wherein cells are grown on glass slides coated with matrix protein.

9. A method of diagnosing interstitial cystitits in an individual, comprising the steps of:
   obtaining primary cultures of uroepithelial cells from bladder biopsies of said individual;
   using primary cultures and a growth medium containing low levels of calcium and growth factors to select urothelial cells of basal type and produce secondary cultures thereof;
   measuring differentiation by probing cells with antibodies against cytokeratin 8, a marker of epithelial differentiation and detecting it by an immunofluorescence microscopy technique;
   determining the percentage of single cells that display intense cytokeratin 8 expression;
   determining the percentage of large colonies that contain more than 6 intense cytokeratin 8-expressing cells;
   comparing percentage of single cells that display intense cytokeratin 8 expression and the percentage of large colonies that contain more than 6 intense cytokeratin 8-expressing cells to that in a sample of similarly cultured urothelial cells taken from an individual not suspected of having interstitial cystitis.

10. The method of claim 9, wherein the calcium in the medium has a concentration of about 0.2 mM.

11. The method of claim 9, wherein said medium contains 0.005% bovine pituitary extract (BPE).

12. The method of claim 9, wherein cells are grown on glass slides coated with matrix protein.

13. A method of diagnosing interstitial cystitis in an individual, comprising the steps of:
   obtaining primary cultures of urothelial cells from bladder biopsies of said individual;
   using primary cultures and a growth medium containing low levels of calcium and growth factors to select urothelial cells of basal type and produce secondary cultures thereof;
   measuring differentiation by probing cells with antibodies against $\beta_1$ subunit of integrins and examining its presence at cell-cell contacts, a marker of epithelial differentiation;
   determining the percentage of large colonies that express $\beta_1$ integrin at cell-cell contacts of 2,3,4,5,6, or more than 6 cells;
   comparing percentage of large colonies that express $\beta_1$ integrin at cell-cell contacts of 2,3,4,5,6, or more than 6 cells to that in a sample of similarly cultured urothelial cells taken from an individual not suspected of having interstitial cystitis.

14. The method of claim 13, wherein the calcium in the medium has a concentration of 0.2 mM.

15. The method of claim 13, wherein said medium contains 0.005bovine pituitary extract (BPE).

16. The method of claim 13, wherein cells are grown on glass slides coated with matrix protein.

17. A method of diagnosing interstitial cystitis in an individual, comprising the steps of:
   obtaining primary cultures of urothelial cells from bladder biopsies of said individual;
   using primary cultures and a growth medium containing low levels of calcium and growth factors to select urothelial cells of basal type and produce secondary cultures thereof;
   measuring differentiation by probing cells with antibodies against cadherins and catenins, proteins that distribute to cell-cell contacts of differentiated epithelial cells and are crucial for normal cell-cell interactions and to examine their presence at cell-cell contacts;
   determining the percentage of large colonies that express cadherins at cell-cell contacts of more than 6 cells;
   determining the percentage of large colonies that express catenins at cell-cell contacts of more than 6 cells
   comparing percentage of large colonies that express cadherins at cell-cell contacts of more than 6 cells to that in a sample of similarly cultured urothelial cells taken from an individual not suspected of having interstitial cystitis; and
   comparing percentage of large colonies that express catenins at cell-cell contacts of more than 6 cells to that in a sample of similarly cultured urothelial cells taken from an individual not suspected of having interstitial cystitis.

18. The method of claim 17, wherein the calcium in the medium has a concentraction of 0.2 mM.

19. The method of claim 17, wherein said medium contains 0.005% bovine pituitary extract (BPE).

20. The method of claim 17, wherein cells are grown on glass slides coated with matrix protein.

21. A method of diagnosing interstitial cystitis in an individual, comprising the steps of:
   obtaining primary cultures of urothelial cells from bladder biopsies of said individual;
   using primary cultures and a growth medium containing low levels of calcium and growth factors to select urothelial cells of basal type and produce secondary cultures thereof;
   double labeling cells with antibodies against nitrotyrosine and phosphotyrosine and examining their presence at cell-cell contacts;
   determining the percentage of large colonies that express phosphotyrosine and/or nitrotyrosine at cell-cell contacts of 2,3,4,5,6, or more than 6 cells;
   determining the ratio of phosphotyrosine:nitrotyrosine expression in these groups of colonies;
   comparing the ratio of phosphotyrosine:nitrotyrosine expression in these groups of colonies to that in a sample of similarly cultured urothelial cells taken from an individual not suspected of having interstitial cystitis.

22. The method of claim 21, wherein the calcium in the medium has a concentration of 0.2 mM and wherein said medium contains 0.005% bovine pituitary extract (BPE).

23. The method of claim 21, wherein cells are grown on glass slides coated with matrix protein.

24. A method of diagnosing interstitial cystitis in an individual, comprising the steps of:
   obtaining primary cultures of urothelial cells from bladder biopsies of said individual;
   using primary cultures and a growth medium containing low levels of calcium and growth factors to select urothelial cells of basal type and produce secondary cultures thereof;

measuring the percentage of apoptotic cells in the entire culture;

measuring the percentage of large colonies that contain 1,2,3,4,5,6, or more than 6 apoptotic cells; and comparing the percentage of said colonies to baseline values of the same parameters determined in samples of similarly cultured urothelial cells taken from individuals not suspected of having interstitial cystitis.

25. The method of claim 24, wherein the calcium in the medium has a concentration of 0.2 mM and wherein said medium contains 0.005% bovine pituitary extract (BPE).

26. The method of claim 24, wherein cells are grown on glass slides coated with matrix protein.

* * * * *

UNITED STATES PATENT AND TRADEMARK OFFICE
CERTIFICATE OF CORRECTION

PATENT NO.   : 5,824,493
DATED        : October 20, 1998
INVENTOR(S)  : Ada Elgavish It is certified that error appears in the above-identified patent and that said Letters Patent is hereby corrected as shown below:

<u>Column 1,</u>
Line 3, please insert the following paragraph before "Background of the Invention":
-- FEDERAL FUNDING
     This invention was produced in part using funds obtained through grant numbers DK44835 and DK47546 from the National Institutes of Health. Consequently, the federal government has certain rights in this invention. --

Signed and Sealed this

Twenty-fourth Day of September, 2002

*Attest:*

*Attesting Officer*

JAMES E. ROGAN
*Director of the United States Patent and Trademark Office*